United States Patent [19]

Yock et al.

[11] Patent Number: 4,887,606
[45] Date of Patent: Dec. 19, 1989

[54] APPARATUS FOR USE IN CANNULATION OF BLOOD VESSELS

[76] Inventors: Paul G. Yock, 25 Cerritos Ave., San Francisco, Calif. 94127; Alan R. Selfridge, 2592 Middlefield Rd., Palo Alto, Calif. 94301

[21] Appl. No.: 296,272

[22] Filed: Jan. 11, 1989

Related U.S. Application Data

[63] Continuation of Ser. No. 908,556, Sep. 18, 1986, abandoned.

[51] Int. Cl.⁴ .............................................. A61B 8/12
[52] U.S. Cl. .......................... 128/662.05; 128/662.06
[58] Field of Search ..................... 128/662.05, 662.06

[56] References Cited

U.S. PATENT DOCUMENTS

| | | | |
|---|---|---|---|
| 3,430,625 | 3/1969 | McLeod | 128/663 |
| 3,556,079 | 1/1971 | Omizo | 128/661 |
| 3,938,502 | 2/1976 | Bom | 128/660 |
| 4,249,539 | 2/1981 | Vilkomerson et al. | 128/660 |
| 4,349,032 | 9/1982 | Koyata | 128/660 |
| 4,407,294 | 10/1983 | Vilkomerson | 128/660 |
| 4,428,379 | 1/1984 | Robbins et al. | 128/660 |
| 4,431,006 | 2/1984 | Trimmer et al. | 128/660 |
| 4,546,771 | 10/1985 | Eggleton et al. | 128/660 |
| 4,576,177 | 3/1986 | Webster, Jr. | 128/660 |
| 4,582,067 | 4/1986 | Silverstein et al. | 128/663 |
| 4,665,925 | 5/1987 | Millar | 128/663 |

OTHER PUBLICATIONS

Hisonaga, K. et al, "A New Trans-Digestive Tract Scanner with a Gastro-Fiber-Scope", Proc. 23rd AIUM 1978, p. 108.
*Attorney's Medicolegal Dictionary*, (Schmidts) Bender Publ. Co., N.Y., ©1980, pp. S-167, S-227, T-128.

*Primary Examiner*—Francis Jaworski
*Attorney, Agent, or Firm*—Flehr, Hohbach, Test, Albritton & Herbert

[57] ABSTRACT

Apparatus for use in cannulation of blood vessels includes a hollow needle having a sharpened end for penetrating tissue, a trocar including a transducer mounted on one end for positioning within the hollow needle for transmitting and receiving ultrasonic waves through the sharpened end of the needle. The trocar further includes a support rod for the transducer and ultrasound damping material attaching the transducer to the support rod. Electrical conductors are provided through the support rod or on the surface of the support rod in contact with electrodes on the front and back surfaces of the transducer for transmitting electrical signals to and from the transducer. A syringe portion is detachably detached from the needle for receiving the back flow of blood when the needle is inserted into a blood vessel.

6 Claims, 2 Drawing Sheets

NEEDLE IN SKIN BEGIN SEARCH FOR VESSEL BY LATERAL SWINGS | ARTERY | VEIN | ADVANCING TO VEIN | PENETRATE VEIN

APPARATUS FOR USE IN CANNULATION OF BLOOD VESSELS

This is a continuation of application Ser. No. 908,556 filed Sept. 18, 1986, and now abandoned.

This invention relates generally to cannulation of arteries and veins, and more particularly the invention relates to use of ultrasonic techniques for flow directed cannulation.

Insertion of arterial and venous catheters for angiography and acute care of patents is a major source of discomfort, morbidity, and even mortality. The problem of accurate location and penetration of arteries and veins is especially acute for patients who may be obese or present unusual anatomy and who are undergoing cardiac catherization and other radiologic procedures such as cerebral angiograms.

The potential utility of Doppler ultrasound for accurately guiding a needle into a vessel has been recognized. Most applications utilize the transmission of ultrasonic waves through the needle and reception of ultrasonic echos by a separate transducer located on the body of the patient and separate from the syringe and needle. Such applications obviously have limited accuracy. U.S. Pat. No. 3,556,079 for "Method of Puncturing a Medical Instrument Under Guidance of Ultrasound" discloses in one embodiment the placement of both transmitting and receiving transducers in the needle and syringe. Such an embodiment, however, requires a special catheter construction and can give an erroneous signal when the needle engages the blood vessel before penetrating the vessel.

SUMMARY OF THE INVENTION

An object of the present invention is improved apparatus using Doppler techniques in cannulation of blood vessels.

Another object of the invention is an ultrasonic needle guide for rapid cannulation of central vessels.

Yet another object of the invention is a Doppler needle and guide that is readily used by physicians familiar with the use of trocars in needle cannulations.

Still another object of the invention is a coaxial electrical connection to a piezoelectric transducer element for signal shielding and enhanced patient safety.

A feature of the invention is the use of a transducer insert positioned within a hollow needle and including an ultrasonic transducer at one end thereof for transmitting and receiving ultrasonic waves through the sharpened end of the needle. Upon location and penetration of a blood vessel, the transducer insert is removable from the needle for implementation of the known Seldinger technique for placing a catheter in the vessel.

The invention and objects and features thereof will be more readily apparent from the following detailed description and appended claims when taken with the drawing.

DETAILED DESCRIPTION OF ILLUSTRATED EMBODIMENTS

Figure 1:
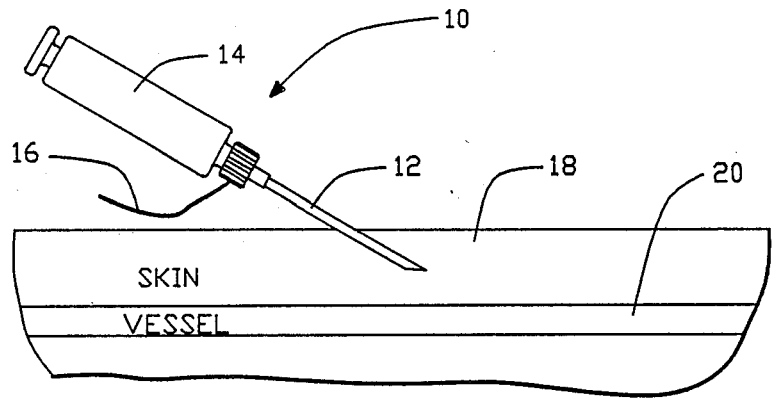
FIG. 1 is a schematic representation of a needle being inserted into tissue for cannulation of a vessel.

Referring now to the drawing, FIG. 1 is a schematic illustration of a syringe assembly shown generally at 10 in accordance with the invention. The assembly 10 includes a needle 12 and a container portion 14 with ultrasonic transducer means within the needle 12 as will be described hereinbelow. Wires 16 are electrically connected with the transducer means for the transmission and reception of electrical signals. In the illustrated schematic, the needle 10 is being inserted through tissue 18 towards a blood vessel 20.

As above described, the insertion of arterial and venous catheters can be a major source of discomfort, morbidity, and even mortality. The assembly in accordance with the present invention and the method of using the assembly more accurately direct the needle to and in penetration with the vessel 20. As the needle 10 is passed through the tissue 18, the tip of the needle is moved in a slight arc for directing ultrasound energy transmitted through the needle to the vessel 20. The returned echo signal is used for accurately guiding the needle 12 to the vessel 20 and may provide an indication of when the needle penetrates the vessel 20.

Figure 2:
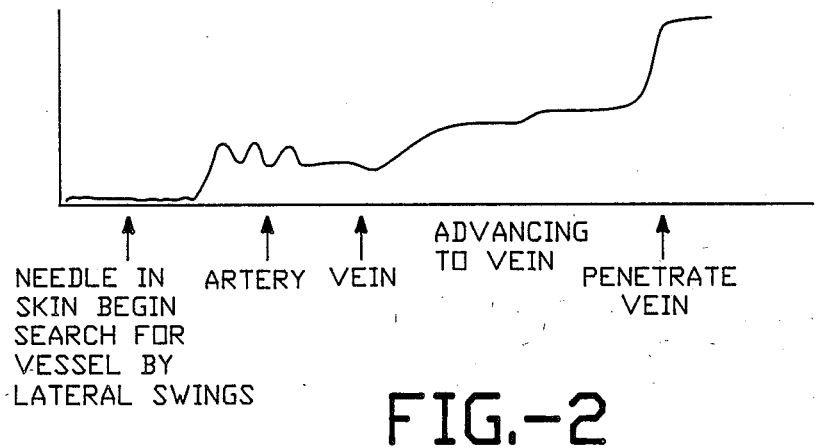
FIG. 2 is a plot of Doppler signal intensity versus distance in tissue of a needle in FIG. 1.

FIG. 2 is a plot of intensity of the Doppler signal versus depth within the tissue 18. When the needle is first inserted into the tissue but not direct towards an artery or vein, the response is small and relatively flat as indicated. Upon pointing the needle at an artery an increased modulated wave is detected; conversely, when the needle is pointed towards a vein an increased generally uniform signal is detected. As the needle is advanced towards the artery or vein, the intensity of the reflected wave increases, and upon penetration of the vessel a stepped increase in the intensity of the reflected signal is indicated. Actual penetration of the vessel will be indicated by the back flow of blood when the vessel is penetrated by maintaining a negative pressure in the needle and a constant back pressure on the syringe while the needle is being advanced. Once the vessel is penetrated, brisk backflow of blood in the needle indicates safe penetration of the vessel and can cause the stepped increase in reflected wave intensity thereby indicating a safe location for injection of medications or passage of a wire into the vessel.

Figure 3:
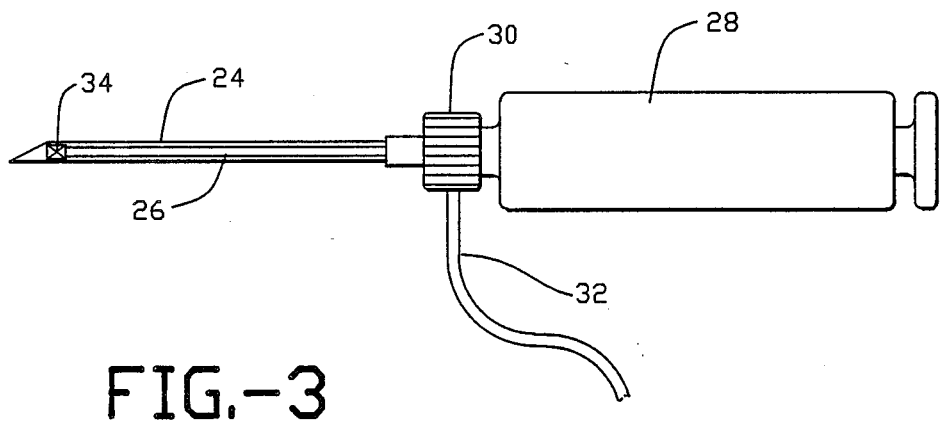
FIG. 3 is a perspective view illustrating cannulation apparatus in accordance with one embodiment of the invention.

FIG. 3 is an illustrative view of apparatus for use in cannulation of blood vessels in accordance with the present invention. The apparatus includes a needle portion 24, shown in section view to illustrate a stylet 26 therein. The needle and stylet are connected to a syringe 28 by means of a connector 30. Electrical wires 32 are interconnected through the stylet with an ultrasonic transducer 34 at one end of the stylet. The transducer 34 is positioned at a sharpened end of the needle 24 for the transmission and reception of ultrasonic energy through the open end of the needle.

Figure 4:
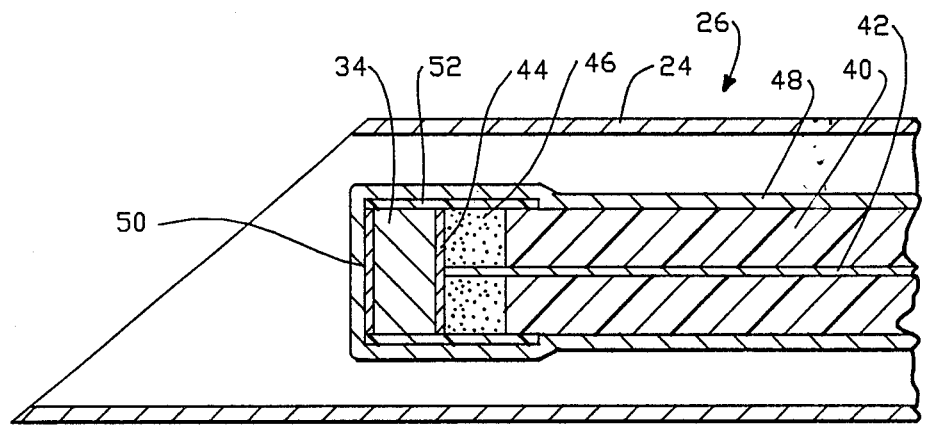
FIG. 4 is a section view of a needle portion and a trocar portion of the apparatus of FIG. 3.
Figure 5:
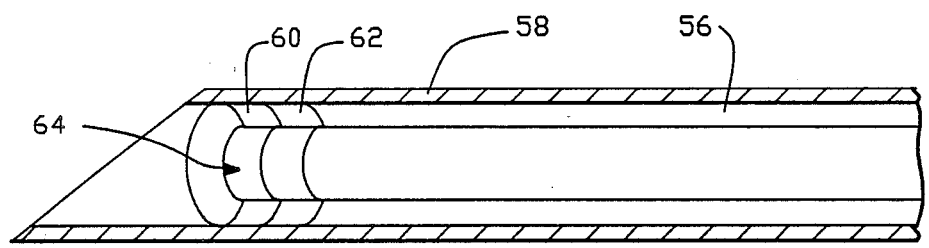

FIG. 4 is a section view of a portion of the needle 24 and the stylet shown generally at 26 further illustrating the construction of the stylet 26 in accordance with a preferred embodiment. The stylet includes a plastic support rod 40 through which a conductor 42 extends into contact with an electrode 44 on the back surface of transducer 34. Transducer 34 is affixed to the support rod 40 by means of a low impedance epoxy 46 which is filled with glass microballoons. A second electrical conductor 48 is formed on the exterior surface of support rod 40 by means of metal deposition and extends into contact with an electrode 50 on a front surface of the transducer 34. The conductors 42 and 48 form a coaxial cable, and the outer shield conductor 48 can be grounded during use. An insulative material 52 such as an epoxy is formed around the periphery of the transducer 34 to electrically isolate the electrode 44 on the back surface from the conductor 48 connected to the electrode 50 on the front surface. The transducer 34 is positioned near the sharpened end of needle 24 for the transmission and reception of energy through the opening in the needle.

In the embodiment of FIG. 4 the stylet 26 has an outer diameter less than the inner diameter of needle 24 (i.e. the stylet is spaced from the needle) whereby blood flow upon penetration of a vessel is accommodated around the stylet. In this embodiment the electrical conductor on the outer surface of the trocar physically and electrically contacts the needle 58, and the needle then functions as one electrode in transmitting energy to the transducer 60 mounted to the trocar by the energy absorbing epoxy 62. Blood flow is accommodated in this embodiment of the invention by removing a portion of the trocar as indicated at 64.

Figure 6:
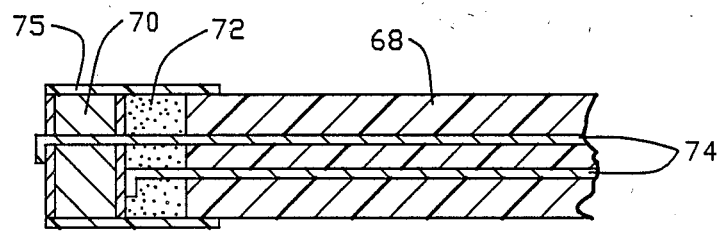
Figure 7:
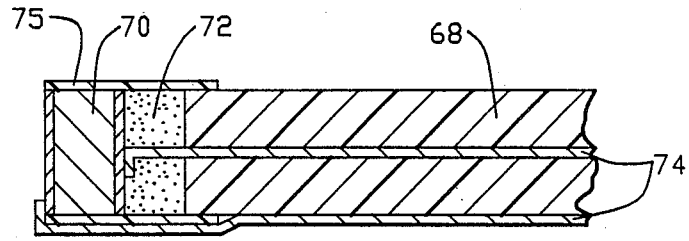

While the preferred embodiment of the invention is illustrated in FIG. 4, other electrode structures are readily fabricated as illustrated in section views of FIGS. 6 and 7. In FIG. 6 a support rod 68 is again provided for supporting the transducer 70 and the backing epoxy 72.

In one embodiment of the invention the following materials were employed:

Support rod—18 gauge stainless steel tubing
Backing material—Emerson IG0101 microballoons in epoxy
Transducer—PZTSA, 1 mm diameter, 20 MHZ
Insulation Material—Ablestix 931-1 epoxy
Electrical Conductive Material—Trabond 2902 silver epoxy The apparatus for cannulation of blood vessels as described above is readily utilized in the Seldinger technique for blood vessel cannulation. After the needle is inserted and guided to a vein by the Doppler techniques, the vein is penetrated as indicated by back flow of blood through the needle to the container portion. The container is then removed from the needle and the connector, and the stylet is then removed from the needle. A wire is placed through the needle into the vein, and the needle is then removed. Finally, a prosthesis is guided into position in the vein by the wire and the wire is then removed.

Apparatus for use in cannulation of blood using Doppler techniques in accordance with the invention has proved to be economically fabricated and readily used by physicians. While the invention has been described with reference to specific embodiments, the description is illustrative of the invention and is not to be construed as limiting the invention. For example, the transducer can be mounted directly to the support rod without the use of damping material. Various modifications and applications may occur to those skilled in the art without departing from the true spirit and scope of the invention as defined by the appended claims.

What is claimed is:

1. Apparatus for use in cannulation of blood vessels comprising
    a hollow needle having a sharpened end for penetrating tissue,
    a stylet positioned within said needle and including an ultrasound transducer at one end for transmitting and receiving ultrasonic waves through the sharpened end of said needle,
    a support rod for supporting said transducer,
    means attaching said transducer to said support rod,
    coaxial electrical conductors associated with said support rod for transmitting electrical signals to and from said transducer, including a wire extending through said support rod electrically connected with a back surface of said transducer, and a metal conductor on the surface of said rod electrically interconnected with a front surface of said transducer, said metal conductor and support rod being spaced from said needle to facilitate back flow of blood when a blood vessel is penetrated, and
    a syringe portion detachably attached to said needle.

2. Apparatus as defined by claim 1 wherein said transducer includes metal contacts on said front and back surfaces of said transducer.

3. Apparatus as defined by claim 1 wherein said means attaching said transducer to said rod includes an ultrasound damping material.

4. For use in apparatus for cannulation of blood vessels, a stylet for positioning within a hollow needle and comprising a support rod, an ultrasound transducer at one end of said support rod for transmitting and receiving ultrasonic waves, means attaching said transducer to said support rod, and coaxial electrical conductors associated with said support rod for transmitting electrical signals to and from said transducer including a wire extending through said support rod in contact with a back surface of said transducer, and a metal conductor on the surface of said rod in contact with a front surface of said transducer.

5. Apparatus as defined by claim 4 wherein said transducer includes metal contacts on said front surface and said back surface.

6. The trocar as defined by claim 4 wherein said means attaching said transducer into said rod includes an ultrasound damping material.

* * * * *